US006806312B2

(12) United States Patent
Sasagawa et al.

(10) Patent No.: US 6,806,312 B2
(45) Date of Patent: Oct. 19, 2004

(54) THERMOPLASTIC RESIN COMPOSITION

(75) Inventors: Masahiro Sasagawa, Yokohama (JP); Katsumi Suzuki, Kawasaki (JP); Toshikazu Hoshina, Yokohama (JP)

(73) Assignee: Asahu Kasei Kabushiki Kaisha, Osaka (JP)

( * ) Notice: Subject to any disclaimer, the term of this patent is extended or adjusted under 35 U.S.C. 154(b) by 0 days.

(21) Appl. No.: 10/362,073

(22) PCT Filed: Jun. 20, 2001

(86) PCT No.: PCT/JP01/05281

§ 371 (c)(1),
(2), (4) Date: Feb. 20, 2003

(87) PCT Pub. No.: WO03/000788

PCT Pub. Date: Jan. 3, 2003

(65) Prior Publication Data

US 2003/0181587 A1 Sep. 25, 2003

(51) Int. Cl.$^7$ ......................... C08L 23/02; C08L 25/04; C08L 71/12

(52) U.S. Cl. ....................................... 525/92 D; 525/98

(58) Field of Search .................................. 525/92 D, 98

(56) References Cited

FOREIGN PATENT DOCUMENTS

| | | | |
|---|---|---|---|
| JP | 43-6636 | | 3/1943 |
| JP | 56-38338 | A | 4/1981 |
| JP | 63-5401 | B2 | 2/1988 |
| JP | 1-174550 | A | 7/1989 |
| JP | 6-192493 | A | 7/1994 |
| JP | 6-192502 | A | 7/1994 |
| JP | 8-59954 | A | 3/1996 |
| JP | 9-12800 | A | 1/1997 |
| JP | 11-12404 | A | 1/1999 |
| JP | 11-12406 | A | 1/1999 |
| JP | 11-012404 | * | 1/1999 |
| JP | 11-012406 | * | 1/1999 |
| JP | 11-71466 | A | 3/1999 |
| JP | 11-071466 | * | 3/1999 |
| JP | 2000-344974 | A | 12/2000 |

* cited by examiner

*Primary Examiner*—Patricia A. Short
(74) *Attorney, Agent, or Firm*—Birch, Stewart, Kolasch & Birch, LLP

(57) ABSTRACT

The invention is to provide a thermoplastic resin composition rich in heat resistance, oil resistance, and thermal aging resistance and excellent in tensile elongation characteristics, by adding a specific partially hydrogenated block copolymer to a styrene resin and/or poly(phenylene ether) resin and an olefin resin. The invention relates to a thermoplastic resin composition which comprises (A) from 95 to 5% by weight of styrene resin and/or poly(phenylene ether) resin, (B) from 5 to 95% by weight of olefin resin, and (C) a partially hydrogenated block copolymer in an amount of from 2 to 30 parts by weight per 100 parts by weight of the sum of ingredients (A) and (B), wherein (C) is a partially hydrogenated block copolymer obtained from a block copolymer which has at least one polymer block X mainly comprising a vinylaromatic compound and at least one polymer block Y mainly comprising a conjugated diene compound and has a combined vinylaromatic compound content of from 30 to 80% by weight and in which the vinyl bond amount in the polymer block Y mainly comprising a conjugated diene compound is from 20% by weight to less than 65% by weight, by hydrogenating from 35% to less than 70% of the double bonds derived from the conjugated diene compounds.

7 Claims, 1 Drawing Sheet

THERMOPLASTIC RESIN COMPOSITION

This application is the national phase under 35 U.S.C. § 371 of PCT International Application No. PCT/JP01/05281 which has an International filing date of June 20, 2001, designated the United States of America.

TECHNICAL FIELD

The present invention relates to a resin composition rich in heat resistance, oil resistance, and thermal aging resistance and excellent in tensile elongation characteristics. More particularly, the invention relates to a thermoplastic resin composition which comprises a styrene resin or poly (phenylene ether) resin, an olefin resin, and a partially hydrogenated block copolymer having a specific structure and is suitable for containers for foods, etc.

BACKGROUND OF THE INVENTION

Styrene resins are extensively used as injection molding materials or sheet-forming materials because they have satisfactory processability and excellent mechanical properties. However, since styrene resins have poor oil resistance and suffer an abrupt decrease in physical property upon contact with oils such as margarine and sesame oil, they have been used in limited applications. It has hence been attempted to mix an olefin resin therewith in order to improve the oil resistance. However, styrene resins have poor compatibility with olefin resins and, hence, the blending necessarily gives a composition which undergoes a separation phenomenon and is brittle.

On the other hand, poly(phenylene ether) resins are excellent in mechanical properties, electrical properties, etc. and are extensively used in applications such as the housings of business machines or apparatus, various industrial parts, and the like. However, these resins are poor in oil resistance and impact resistance and attempts are being made to mix an olefin resin therewith in order to improve these properties. However, the two kinds of resins are poorly compatible with each other, resulting in a separation phenomenon.

For overcoming those problems, various compositions containing a block copolymer added thereto have been proposed. For example, Japanese Patent Laid-Open No. 38338/1981 proposes a composition comprising a polyolefin resin and a polystyrene resin and containing a hydrogenated block copolymer obtained by hydrogenating a block copolymer having at least one vinylaromatic compound polymer block A and at least one conjugated diene polymer block B to such a degree that at least 70% of the double bonds in the block copolymer are saturated. Specifically, the hydrogenated block copolymers disclosed therein include, for example, one obtained by hydrogenating an A-B type block copolymer having a combined styrene content of 50% and a vinyl content before hydrogenation of 13% so as to hydrogenate 92% of the double bonds. In Japanese Patent Laid-Open No. 174550/1989 also is proposed a composition comprising a polyolefin resin and a polystyrene resin and containing a similar hydrogenated block copolymer. Specifically, the hydrogenated block copolymers disclosed therein include, for example, one obtained by hydrogenating an A-B type block copolymer having a combined styrene content of 35% and a vinyl content in isoprene before hydrogenation of 8% so as to hydrogenate 93% of the double bonds. However, the hydrogenated block copolymers used in these compositions are ones having a high degree of hydrogenation and have had a problem that their productivity is low. For example, the hydrogenation period necessary for obtaining the hydrogenated block copolymer disclosed in Japanese Patent Laid-Open No. 38338/1981 is 6 hours, while the hydrogenation period necessary for obtaining the hydrogenated block copolymer disclosed in Japanese Patent Laid-Open No. 174550/1989 is 8 hours. Namely, considerable time has been required. There has hence been a desire for a polymer which is a block copolymer easy to produce with satisfactory productivity and has excellent properties when added to a composition comprising a polyolefin resin and a polystyrene resin. In addition, the compositions disclosed in those references are insufficient in tensile elongation characteristics although they have been improved in compatibility between the polyolefin resin and polystyrene resin. A further improvement is hence desired.

Furthermore, Japanese Patent Laid-Open No. 12800/1997 proposes a composition comprising a polypropylene resin and poly(phenylene ether) and containing a hydrogenated block copolymer obtained by hydrogenating to from 65 to 80% a block copolymer having a vinylaromatic compound polymer block A and a conjugated diene polymer block B having a large vinyl bond amount. Specifically, the hydrogenated block copolymers disclosed therein include, for example, one obtained by hydrogenating an A-B type block copolymer having a combined styrene content of 60% and a vinyl content before hydrogenation of 74% so as to hydrogenate 68% of the double bonds. However, since the hydrogenated block copolymer used here contains a conjugated diene polymer having a large vinyl amount, the composition has had a drawback that it has poor resistance to thermal aging at high temperatures.

An object of the invention is to provide a thermoplastic resin composition rich in heat resistance, oil resistance, and thermal aging resistance and excellent in tensile elongation characteristics by adding a partially hydrogenated block copolymer having a specific structure to a styrene resin and/or poly(phenylene ether) resin and an olefin resin.

DISCLOSURE OF THE INVENTION

The present inventors made intensive investigations in order to obtain a block copolymer which, when used in blending a styrene resin or poly(phenylene ether) resin with an olefin resin, gives a resin composition rich in heat resistance, oil resistance, and thermal aging resistance and excellent in tensile elongation characteristics and which has satisfactory productivity. As a result, it has been found that the aim can be accomplished by adding a partially hydrogenated block copolymer having a specific structure to a styrene resin and/or poly(phenylene ether) resin and an olefin resin. The invention has thus been completed.

Namely, the invention relates to a resin composition which comprises (A) from 95 to 5% by weight of styrene resin and/or poly(phenylene ether) resin, (B) from 5 to 95% by weight of olefin resin, and (C) a partially hydrogenated block copolymer in an amount of from 2 to 30 parts by weight per 100 parts by weight of the sum of ingredients (A) and (B), wherein (C) is a partially hydrogenated block copolymer obtained by hydrogenating a block copolymer which has at least one polymer block X mainly comprising a vinylaromatic compound and at least one polymer block Y mainly comprising a conjugated diene compound and has a combined vinylaromatic compound content of from 30 to 80% by weight and in which the vinyl bond amount in the conjugated dienes before hydrogenation is from 20% by weight to less than 65% by weight to thereby saturate from 35% to less than 70% of the double bonds derived from the conjugated diene compounds in the block copolymer.

BEST MODE FOR CARRYING OUT THE INVENTION

Figure 1:
FIG. 1 is an example of a transmission electron photomicrograph of the thermoplastic resin composition of Example 1 according to the invention. The hydrogenated block copolymer (black streak layers) is mostly present at the boundary between the propylene resin phase (undyed bright phase) and the styrene resin phase (dyed dark phase).

The invention will be explained below in detail.

Examples of the styrene resin to be used as or in ingredient (A) in the invention include homopolymers or copolymers of styrene, methylstyrene, ethylstyrene, isopropylstyrene, dimethylstyrene, p-methylstyrene, chlorostyrene, bromostyrene, vinylxylene, and the like, styrene/maleic anhydride copolymers, styrene/acrylic acid copolymers, styrene/acrylic ester copolymers, styrene/methacrylic acid copolymers, styrene/acrylonitrile copolymers, acrylonitrile/butadiene/styrene copolymers, and the like. It is also possible to use an impact-resistant polystyrene resin obtained by mixing or graft-polymerizing a rubber such as a butadiene rubber, styrene/butadiene rubber, or ethylene/propylene rubber with the styrene resin. Especially preferred is polystyrene or the rubber-modified impact-resistant polystyrene. The melt flow rate (MFR; 200° C., 5-kg load) of the styrene resin in the invention is preferably from 0.5 to 20 g/10 min, more preferably from 1 to 10 g/10 min.

The poly(phenylene ether) resin (hereinafter abbreviated simply as PPE) as or in ingredient (A) in the invention is a poly(phenylene ether) having structures represented by the following formula (1).

Combined Unit:

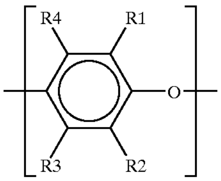

(1)

It is a homopolymer and/or copolymer which comprises units of the above formula (wherein R1, R2, R3, and R4 may be the same or different and each represent a member selected from the group consisting of hydrogen, halogens, primary or secondary, lower alkyl groups having 1 to 7 carbon atoms, a phenyl group, haloalkyl groups, aminoalkyl groups, hydrocarbonoxy groups, and halohydrocarbonoxy groups in which the halogen atom is separated from the oxygen atom by at least two carbon atoms) and has a reduced viscosity (0.5 g/dL; chloroform solution; 30° C.) in the range of from 0.15 to 0.70, more preferably in the range of from 0.20 to 0.60.

Specific examples of the PPE include poly(2,6-dimethyl-1,4phenylene ether), poly(2-methyl-6-ethyl-1,4phenylene ether), poly(2-methyl-6-phenyl-1,4-phenylene ether), poly (2,6-dichloro-1,4-phenylene ether), and the like. Examples thereof further include poly(phenylene ether) copolymers such as copolymers of 2,6-dimethylphenol and another phenol (e.g., 2,3,6-trimethylphenol or 2-methyl-6-butylphenol). Especially preferred of these PPE's is poly(2, 6-dimethyl-1,4phenylene ether). Such PPE's are not particularly limited as long as they are ones obtained by known methods. For example, a PPE can be easily produced by the oxidative polymerization of, e.g., 2,6-xylenol using as a catalyst the cuprous chloride/amine complex of Hay disclosed in the specification of U.S. Pat. No. 3,306,874. Besides this, the method described in, e.g., Japanese Patent Laid-Open No. 152628/1988 can be used to easily produce a PPE. Besides being any of the PPE's described above, the PPE to be used in the invention may be a modified PPE obtained by reacting the PPE with an α,β-unsaturated carboxylic acid or a derivative thereof in the presence or absence of a radical generator at a temperature of from 80 to 350° while keeping the reactants in a molten state, solution state, or slurry state. Furthermore, a mixture of the PPE described above and the modified PPE in any desired proportion may also be used.

Ingredient (A) in the invention more preferably is a styrene resin. Especially preferred of such resins are polystyrene and the impact-resistant polystyrene.

The olefin resin to be used as ingredient (B) in the invention is not particularly limited as long as it is a resin obtained by polymerizing one or more α-olefins, e.g., ethylene, propylene, 1-butene, isobutylene, 4-methyl-1-pentene, and the like. In the case of a copolymer, it may be either a random copolymer or a block copolymer. The resin may contain a thermoplastic olefin elastomer such as, e.g., a copolymer rubber formed from two or more α-olefins or a copolymer of an α-olefin and other monomer(s). Examples of such copolymer rubbers include an ethylene/propylene copolymer rubber (EPR), ethylene/butene copolymer rubber (EBR), ethylene/propylene/diene copolymer rubber (EPDM), and the like. Preferred of these is a polypropylene which is a homopolymer or block polymer. In particular, use of a syndiotactic polypropylene homopolymer or a propylene/ethylene block—block resin having a crystal fusion peak temperature as measured by DSC of 155° C. or higher gives a composition having enhanced heat resistance. The melt flow rate (MFR; 230° C., 2.16 kg load) of the olefin resin in the invention is preferably from 0.5 to 60 g/10 min, more preferably from 1 to 20 g/10 min. In case where the melt flow rate thereof is lower than 0.5 g/10 min, the composition obtained has poor moldability. In case where it exceeds 60 g/10 min, impact resistance decreases.

The partially hydrogenated block copolymer to be used as ingredient (C) in the invention is a partially hydrogenated block copolymer obtained by hydrogenating a block copolymer which has at least one polymer block X mainly comprising a vinylaromatic compound and at least one polymer block Y mainly comprising a conjugated diene compound and has a combined vinylaromatic compound content of from 30 to 80% by weight and in which the vinyl bond amount in the conjugated dienes before hydrogenation is from 20% by weight to less than 65% by weight to thereby saturate from 35% to less than 70% of the double bonds derived from the conjugated diene compounds in the block copolymer.

The polymer block X mainly comprising a vinylaromatic compound is a polymer block which comprises a vinylaromatic compound and a conjugated diene compound in a weight ratio in the range of from 100/0 to 60/40, preferably from 100/0 to 80/20. In the case of a block formed by the copolymerization of a vinylaromatic compound with a conjugated diene compound, the distribution of the conjugated diene compound in this block may be any of a random, taper (distribution in which the monomer units increase or decrease along the molecular chain), or partial block distribution or any desired combination of these. One or more vinylaromatic compounds to be subjected to the polymerization are selected from styrene, alkylstyrenes such as α-methylstyrene, p-methylstyrene, p-tert-butylstyrene, and the like, p-methoxystyrene, vinylnaphthalene, 1,1-diphenylethylene, divinylbenzene, and the like. Preferred of these is styrene.

Furthermore, the polymer block Y mainly comprising a conjugated diene compound is a polymer block which comprises a conjugated diene compound and a vinylaromatic compound in a weight ratio in the range of from 100/0 to 60/40, preferably from 100/0 to 80/20. In the case of a block formed by the copolymerization of a conjugated diene compound with a vinylaromatic compound, the distribution of the vinylaromatic compound in this block may be any of a random, taper (distribution in which the monomer units increase or decrease along the molecular chain), or partial block distribution or any desired combination of these. One or more conjugated diene compounds to be subjected to the polymerization are selected from butadiene, isoprene, piperylene, methylpentadiene, phenylbutadiene, 3,4-dimethyl-1,3-hexadiene, 4,5-diethyl-1,3-octadiene, and the like. Preferred of these is butadiene and/or isoprene.

The molecular structure of the block copolymer described above may be any of linear, branched, and radial structures or a combination of these or the like. However, linear structures are preferred. Especially preferred of these are structures containing two or more X's, in particular, an X-Y-X structure. The blocks X's or blocks Y's may have the same structure or may differ in monomer unit content, their distribution in the molecular chain, molecular weight of the block, or structure such as microstructure. For example, the structure may be one in which the two terminal X's differ in molecular weight, i.e., X-Y-X'.

The vinylaromatic compound content of the partially hydrogenated block copolymer (C) is from 30 to 80% by weight, preferably from 40 to 75% by weight, more preferably from 45 to 70% by weight. In case where the vinylaromatic compound content thereof is lower than 30% by weight, the block copolymer has an insufficient affinity for the styrene resin and/or PPE (ingredient A) and the amount of the block copolymer present at the interface between the ingredient A phase and the ingredient B (olefin resin) phase becomes insufficient, resulting in a poor compatibilizing effect. On the other hand, in case where the content exceeds 80% by weight, affinity for ingredient A becomes so high that the block copolymer is incorporated into the A phase, resulting also in an insufficient compatibilizing effect.

The vinyl bond amount in the partially hydrogenated block copolymer (C) before hydrogenation is from 20% by weight to less than 65% by weight, preferably from 25 to 60% by weight, more preferably from 30 to 55% by weight. The term vinyl bond amount herein means the proportion of 1,2-bonds and 3,4-bonds in the conjugated diene compound which has been incorporated in the bond forms of 1,2-bond, 3,4-bond, and 1,4-bond in the block copolymer. In case where the vinyl bond amount before hydrogenation is less than 20% by weight, the block copolymer has an insufficient affinity for ingredient B and the compatibilizing effect becomes insufficient. As a result, the degree of interfacial presence of the block copolymer decreases and the composition has low tensile elongation. On the other hand, in case where the amount thereof exceeds 65% by weight, affinity for ingredient B becomes so high that the block copolymer is incorporated into the ingredient B phase and the compatibilizing effect hence becomes insufficient in this case also. As a result, the degree of interfacial presence of the block copolymer decreases and the composition obtained has low rigidity and reduced elongation. Furthermore, when a block copolymer having a large vinyl bond amount before hydrogenation is used, the composition has impaired thermal aging resistance and cannot be subjected to recycling or the like.

The partially hydrogenated block copolymer to be used in the invention is obtained by hydrogenating the block copolymer described above to thereby saturate from 35% to less than 70% of the double bonds derived from the conjugated diene compound in the block copolymer. In case where the degree of hydrogenation is lower than 35%, the block copolymer has a reduced affinity for ingredient B and, hence, the block copolymer is incorporated into the ingredient A phase to show an insufficient compatibilizing effect. As a result, the composition has low tensile elongation. This composition further has impaired thermal aging resistance and cannot be subjected to recycling or the like. In case where the degree of hydrogenation is 70% or higher, not only processability is poor but also the partially hydrogenated block copolymer has lower productivity than ones having degrees of hydrogenation lower than 70%. In the partially hydrogenated block copolymer to be used in the invention, the residual vinyl bond amount is preferably less than 10%, more preferably 5% or less, even more preferably 3% or less. The term residual vinyl bond amount herein means the amount of vinyl bonds remaining unhydrogenated per 100 initial conjugated diene units. In case where the residual vinyl bond amount in the block copolymer is 10% or larger, the compatibilizing effect becomes insufficient and the composition obtained has poor thermal aging properties.

In the partially hydrogenated block copolymer (C), the weight-average molecular weight of the polymer block X mainly comprising a vinylaromatic compound is preferably from 5,000 to 50,000 and that of the polymer block Y mainly comprising a conjugated diene compound is preferably from 5,000 to 70,000. Molecular weights of the polymer block X lower than 5,000 result in a reduced affinity for ingredient A, while molecular weights of the polymer block Y lower than 5,000 result in a reduced affinity for ingredient B and a poor compatibilizing effect. In case where the molecular weight of the polymer block X exceeds 50,000 or the molecular weight of the polymer block Y exceeds 70,000, the block copolymer has an increased melt viscosity because of the too high molecular weight of the block copolymer and is insufficiently dispersed in a resin composition comprising ingredient A and ingredient B, resulting in a poor compatibilizing effect.

The melt flow rate (MFR; 230° C., 2.16 kg load) of the partially hydrogenated block copolymer (C) is preferably from 0.1 to 50 g/10 min, more preferably from 0.5 to 20 g/10 min, even more preferably from 1 to 10 g/10 min. In case where the melt flow rate thereof is lower than 0.1 g/10 min, the melt viscosity is too high to obtain a sufficient compatibilizing effect. In case where it exceeds 50 g/10 min, the effect of reinforcing the interface between ingredient A and ingredient (B) decreases.

Processes for producing the partially hydrogenated block copolymer (C) are not particularly limited and known methods may be employed. For example, a block copolymer can be produced by polymerizing a vinylaromatic compound and a conjugated diene compound in an inert solvent using the technique of living anionic polymerization described in Japanese Patent Publication No. 19286/1961, which uses an organolithium catalyst. Examples thereof include: a method in which a monolithium compound such as n-butyllithium, sec-butyllithium, or tert-butyllithium is used as an organolithium catalyst to successively polymerize the monomers in the order of X, Y, and X to thereby form blocks; a method in which an X-Y type living block copolymer is formed in the order of X-Y and a triblock copolymer of an X-Y-X structure is then formed using a bifunctional coupling agent; a method in which a dilithium compound is used to polymerize the monomers in the order of X and Y to form a triblock copolymer of an X-Y-X structure; and the like. The vinylaromatic compound content is regulated by controlling the composition of feed monomers comprising a vinylaromatic compound and a conjugated diene compound. The amount of vinyl bonds derived from a conjugated diene compound is regulated by using a vinyl amount regulator. Examples of the vinyl amount regulator include amines such as N,N,N',N'-tetramethylethylenediamine, trimethylamine, triethylamine, and diazobicyclo[2,2,2]octane, ethers such as tetrahydrofuran, diethylene glycol dimethyl ether, and diethylene glycol dibutyl ether, thioethers, phosphines, phosphoramides, alkylbenzenesulfonic acid salts, alkoxides of potassium or sodium, and the like.

The block copolymer thus obtained is subjected to a hydrogenation reaction by a known method, whereby the partially hydrogenated block copolymer is obtained. Known catalysts for use in the hydrogenation reaction include (1) a supported type heterogeneous catalyst and (2) a Ziegler catalyst or a homogeneous catalyst comprising a titanocene compound. Specifically, a predetermined amount of hydrogen is added in an inert solvent in the presence of a hydrogenation catalyst, for example, by the method described in Japanese Patent Publication No. 6636/1968 or Japanese Patent Publication No. 5401/1988, whereby a solution of a partially hydrogenated block copolymer can be obtained.

From the thus-obtained solution of a partially hydrogenated block copolymer, the partially hydrogenated block copolymer can be obtained by removing the solvent by an ordinary method. According to need, a deashing step for metal removal can be employed. Furthermore, a terminator, antioxidant, neutralizer, surfactant, and the like may be used according to need.

In particular, it is preferred in the composition of the invention that 50% or more, preferably 60% or more, of the partially hydrogenated block copolymer (C) be present at the boundary between the styrene resin or poly(phenylene ether) resin (A) and the olefin resin (B). When the degree of the presence is 50% or higher, the strength of interfacial adhesion between the styrene resin or poly(phenylene ether) resin and the olefin resin is excellent and, hence, excellent performance is exhibited with respect to tensile elongation characteristics.

The proportions in which the ingredients according to the invention are blended are as follows. The blending ratio of the styrene resin and/or poly(phenylene ether) resin (ingredient A) to the olefin resin (ingredient B) is from 95:5 to 5:95 by weight. It is possible to regulate the ratio in such a manner that the proportion of ingredient A is increased for enhancing rigidity and the proportion of ingredient B is increased when heat resistance and oil resistance are important. However, from the standpoint of balancing rigidity with heat resistance and oil resistance, the blending ratio of ingredient A to ingredient B is preferably from 80:20 to 40:60 by weight.

The amount of the partially hydrogenated block copolymer (C) to be added is from 2 to 30 parts by weight, preferably from 5 to 15 parts by weight, per 100 parts by weight of the sum of the styrene resin and/or poly(phenylene ether) resin (ingredient A) and the olefin resin (ingredient B). In case where the amount thereof is less than 2 parts by weight, the compatibilizing effect is insufficient. On the other hand, amounts thereof exceeding 30 parts by weight not only result in reduced rigidity but are uneconomical.

Any desired additives can be incorporated into the thermoplastic resin composition of the invention according to need. The additives are not particularly limited in kind as long as they are ones generally used for incorporation into resins. Examples thereof include inorganic fillers such as silica, calcium carbonate, magnesium carbonate, calcium sulfate, and talc, organic fibers, pigments such as titanium oxide, carbon black, and iron oxide, lubricants or release agents such as stearic acid, behenic acid, zinc stearate, calcium stearate, magnesium stearate, and ethylenebisstearamide, plasticizers such as organic polysiloxanes and mineral oils, antioxidants such as hindered phenol compounds and phosphorus compounds, flame retardants, ultraviolet absorbers, antistatic agents, reinforcements such as glass fibers, carbon fibers, and metal whiskers, other additives, mixtures of these, and the like.

Processes for producing the resin composition of the invention are not particularly limited and known methods can be used. For example, use may be made of: a melt kneading method using a general mixing machine such as a Banbury mixer, single-screw extruder, twin-screw extruder, co-kneader, multi-screw extruder, or the like; a method in which the ingredients are dissolved or dispersed/mixed and the solvent is then removed with heating; or the like. Preferably, the ingredients are kneaded at 180° C. or higher, preferably 200° C. or higher, and a shear rate of 100 $sec^{-1}$, which are conditions under which the styrene resin or poly(phenylene ether) resin (A), olefin resin (B), and partially hydrogenated block copolymer (C) are sufficiently dissolved and mixed and the partially hydrogenated block copolymer (C) moves to the interface between the (A) phase and the (B) phase. Methods in which a twin-screw extruder is used are preferred. A preferred molding method in utilizing the resin composition of the invention is to temporarily knead ingredients by any of those methods to produce master pellets and subject the pellets to molding or optionally to foam molding.

EXAMPLES

The present invention will be illustrated in greater detail with reference to the following Examples, but the invention should not be construed as being limited thereto.

(1) Ingredients to be Used and Production Thereof (a) Styrene Resin

Commercial impact-resistant polystyrene resin: 475D (manufactured by A & M Styrene Co., Ltd.)

(b) Olefin Resins (b-1) Propylene Resin

Commercial homopolypropylene resin: PL 500A (manufactured by Montel SDK Sunrise Co., Ltd.)

(b-2) Ethylene Resin

Commercial high-density polyethylene resin: Suntec J301 (manufactured by Asahi Chemical Industry Co., Ltd.)

(c) Block Copolymers i) An autoclave having a capacity of 100 L and equipped with a stirrer and a jacket was cleaned, dried, and subjected to nitrogen displacement. Thereinto was introduced a cyclohexane solution containing 33 parts by weight of styrene purified beforehand. Subsequently, n-butyllithium and tetramethylethylenediamine were added and the styrene was polymerized at 70° C. for 1 hour. Thereafter, a cyclohexane solution containing 34 parts by weight of butadiene purified beforehand was added and the butadiene was polymerized for 1 hour. Furthermore, a cyclohexane solution containing 33 parts by weight of styrene was added and the styrene was polymerized for 1 hour.

The block copolymer solution obtained was sampled, and 0.3 parts by weight of octadecyl 3-(3,5-di-t-butyl-4-hydroxyphenyl)propionate was added to the sample per 100 parts by weight of the block copolymer. Thereafter, the solvent was removed with heating (the copolymer obtained is referred to as polymer I). Polymer I had a styrene content of 66% by weight, a 1,2-vinyl bond amount in the polybutadiene part of 50% by weight, and a number-average molecular weight of 56,000.

Incidentally, styrene content was determined by infrared spectroscopy (IR). Vinyl bond amount was determined through analysis by infrared spectroscopy (IR) and calculation by the Hampton method. Number-average molecular weight was measured by gel permeation chromatography (GPC).

Subsequently, the remaining block copolymer solution was subjected to hydrogenation at a temperature of 70° C. using di-p-trisbis(1-cyclopentadienyl)titanium and n-butyllithium as a hydrogenation catalyst. The result polymer solution was sampled to obtain polymer II. Polymer II had a degree of hydrogenation of 26%. Incidentally, the degree of hydrogenation was determined with a nuclear magnetic resonance apparatus (NMR). The degree of hydrogenation was controlled by measuring with a flow meter the amount of hydrogen gas which was being fed and stopping the gas feeding at the time when the predetermined hydrogenation degree was reached. The remaining polymer solution was subjected to hydrogenation again to obtain copolymer solutions of polymers III and IV. Polymer III had a degree of hydrogenation of 44% and the time period required after initiation of the hydrogenation was 30 minutes. Polymer IV had a degree of hydrogenation of 65% and the time period required after initiation of the hydrogenation was 45 minutes.

In the same manner as for polymer I, each copolymer solution was subjected to stabilizer addition and then to solvent removal with heating. Thus, various polymers (II to IV) were produced. The polymer structure of each sample is shown in Table 1.

ii) A block copolymer was obtained in the same manner as in i) above, except that the amount of styrene to be charged and the amounts of n-butyllithium and tetramethylethylenediamine to be added were changed. The polymer obtained had a styrene content of 60% by weight, a 1,2-vinyl bond amount in the polybutadiene part of 25% by weight, and a number-average molecular weight of 76,000 (referred to as polymer V).

Furthermore, the block copolymer solution was subjected to hydrogenation in the same manner as in i) above to produce polymer VI. The polymer structure of each sample is shown in Table 1.

iii) A block copolymer was obtained in the same manner as in ii) above, except that tetramethylethylenediamine was not added. The polymer obtained had a styrene content of 60% by weight, a 1,2-vinyl bond amount in the polybutadiene part of 12% by weight, and a number-average molecular weight of 74,000.

Furthermore, the block copolymer solution was subjected to hydrogenation in the same manner as in i) above to produce polymers VII and VIII. The polymer structure of each sample is shown in Table 1.

iv) A block copolymer was obtained in the same manner as in i) above, except that the amount of styrene to be charged and the amounts of n-butyllithium and tetramethylethylenediamine to be added were changed. The polymer obtained had a styrene content of 50% by weight, a 1,2-vinyl bond amount in the polybutadiene part of 40% by weight, and a number-average molecular weight of 62,000 (referred to as polymer IX).

Furthermore, the block copolymer solution was subjected to hydrogenation in the same manner as in i) above to produce polymers X and XI. The polymer structure of each sample is shown in Table 1.

v) A block copolymer was obtained in the same manner as in i) above, except that the amount of styrene to be charged first was changed to 37 parts by weight and the amount of styrene to be charged after the butadiene polymerization was changed to 29 parts by weight. The polymer obtained had a styrene content of 66% by weight, a 1,2-vinyl bond amount in the polybutadiene part of 48% by weight, and a number-average molecular weight of 54,000.

Furthermore, the block copolymer solution was subjected to hydrogenation in the same manner as in i) above to produce polymer XII. The polymer structure is shown in Table 1.

vi) An autoclave having a capacity of 100 L and equipped with a stirrer and a jacket was cleaned, dried, and subjected to nitrogen displacement. Thereinto was introduced a cyclohexane solution containing 30 parts by weight of styrene purified beforehand. Subsequently, n-butyllithium and tetramethylethylenediamine were added and the styrene was polymerized at 70° C. for 1 hour. Thereafter, a cyclohexane solution containing 40 parts by weight of isoprene purified beforehand was added and the isoprene was polymerized for 1 hour. Furthermore, a cyclohexane solution containing 30 parts by weight of styrene was added and the styrene was polymerized for 1 hour.

The block copolymer solution obtained was sampled, and 0.3 parts by weight of octadecyl 3-(3,5-di-t-butyl-4-hydroxyphenyl)propionate was added to the sample per 100 parts by weight of the block copolymer. Thereafter, the solvent was removed with heating (the copolymer obtained is referred to as polymer XIII). Polymer XIII had a styrene content of 60% by weight, a total vinyl bond amount in the polyisoprene part of 40% by weight, and a number-average molecular weight of 52,000.

Subsequently, the remaining block copolymer solution was subjected to hydrogenation at a temperature of 70° C. using di-p-trisbis(1-cyclopentadienyl)titanium and dibutylmagnesium as a hydrogenation catalyst to obtain polymer XIV. Polymer XIV had a degree of hydrogenation of 52%. The remaining polymer solution was subjected to hydrogenation again to obtain a copolymer solution of polymer XV. Polymer XV had a degree of hydrogenation of 92%. The polymer structure of each sample is shown in Table 1.

vii) A block copolymer was obtained in the same manner as in ii) above, except that the amount of tetramethylethylenediamine to be added was increased. The polymer obtained had a styrene content of 60% by weight, a 1,2-vinyl bond amount in the polybutadiene part of 74% by weight, and a number-average molecular weight of 78,000.

Furthermore, the block copolymer solution was subjected to hydrogenation in the same manner as in i) above to produce polymer XVI. The polymer structure is shown in Table 1.

(2) Preparation of Resin Compositions and Property Measurements

Ingredient (a), ingredient (b), and ingredient (c) were mixed together according to the formulations shown in Table 2 and Table 3. Each mixture was melt-kneaded with a 30-mm twin-screw extruder at a temperature of 220° C. and pelletized. Incidentally, the properties shown in the Examples and Comparative Examples were measured according to the following standards and test methods. The pellets obtained were injection-molded at 220° C. and examined for the following various properties 1 to 4.

1. Tensile Elongation Characteristics:

An injection-molded test piece was examined for tensile elongation at break in accordance with ASTM D638. The pulling rate was 5 mm/min.

2. Heat Resistance:

An injection-molded test piece was examined for Vicat softening point under a load of 1 kgf in accordance with ASTM D1525. The softening point was used as an index.

3. Rigidity:

An injection-molded test piece was subjected to a bending test to determine the flexural modulus in accordance with ASTM D790.

4. Degree of Interfacial Presence of Block Copolymer:

The proportion of the block copolymer present at the boundary between the styrene resin phase and the olefin resin phase to all the copolymer incorporated was measured and calculated by the following method.

An ultrathin section is cut out of an injection-molded object of a resin composition with an ultramicrotome along a plane parallel to the direction of resin flow during the molding. The section is dyed with ruthenium tetroxide and a photograph thereof is taken with a transmission electron microscope at a magnification of 10,000 diameters. This photograph is subjected to image analysis to measure the area of the block copolymer present in the styrene resin phase or olefin resin phase and calculate the proportion thereof (a) to all the area over which the image analysis has been made. Furthermore, when the proportion by weight of the block copolymer calculated from the formulation for the resin composition is shown by (b), then the proportion (c) of the block copolymer present at the boundary between the styrene resin phase and the olefin resin phase is defined by ((b)−(a))/(b)×100%. This value was used as an index.

5. Oil Resistance:

A resin composition was molded into a 1 mm-thick sheet with a sheet extruder. The sheet was formed into a container having dimensions of 2 cm high×10 cm long ×10 cm wide, and a synthetic coconut oil was applied to the inner surface thereof. Thereafter, the container was heated with an oven for 1 hour to determine the heating temperature which resulted in a container internal-volume change of 10%. The higher the value of this temperature, the more the oil resistance was judged satisfactory.

6. Thermal aging resistance: When a resin composition was injection-molded, the composition was allowed to reside in the molding machine at a temperature of 240° C. for 10 minutes and then injection-molded into a plate. The surface state of the plate was visually examined and judged. The surface state was evaluated in three grades based on flash development.

A (none)<B (slightly present)<C (present)

7. Processability: A pellet of a resin composition was examined for MFR (200° C./5-kg load). This value of MFR was used as an index thereto.

The results in the following Examples 1 to 7 are shown in Table 2.

Examples 1 to 3

Examples 1 to 3 are examples of a resin composition of the invention comprising 70% by weight impact-resistant polystyrene as ingredient (a), 30% by weight propylene homopolymer (b-1) as ingredient (b), and a partially hydrogenated block copolymer as ingredient (c). It can be seen that these resin compositions not only have high tensile elongation characteristics and high rigidity but also are excellent in heat resistance, oil resistance, and thermal aging resistance.

Examples 4 and 5

Examples 4 and 5 are examples of a resin composition of the invention comprising 45% by weight impact-resistant polystyrene as ingredient (a), 55% by weight propylene homopolymer (b-1) as ingredient (b), and a partially hydrogenated block copolymer as ingredient (c). It can be seen that these resin compositions not only have high tensile elongation characteristics and high rigidity but also are excellent in heat resistance, oil resistance, and thermal aging resistance.

Examples 6 and 7

Examples 6 and 7 are examples of the same composition as in Examples 1 to 3. However, Example 6 is an example in which use was made of a partially hydrogenated block copolymer in which the two terminal blocks differed in styrene content, while Example 7 is an example in which isoprene was used as a conjugated diene compound. These resin compositions each not only have high tensile elongation characteristics and high rigidity but also are excellent in heat resistance, oil resistance, and thermal aging resistance, as in the other Examples.

Furthermore, the MFR of Example 7 was measured and, as a result, was found to be 5.5 g/10 min. In contrast, a resin composition prepared using polymer XV, which had a higher degree of hydrogenation, in place of polymer XIV, which was used in Example 7, had an MFR of 4.9 g/10 min. It can be seen that the resin composition of the invention is superior in processability.

That the resin compositions of the invention have excellent properties is understood more clearly when these compositions are compared with the following Comparative Examples. The results in the following Comparative Examples 1 to 9 are shown in Table 3.

Comparative Example 1

Comparative Example 1 is an example of a resin composition comprising 70% by weight impact-resistant polystyrene and 30% by weight propylene homopolymer and containing no partially hydrogenated block copolymer. This composition has poor compatibility and is considerably inferior not only in tensile elongation characteristics but in oil resistance.

Comparative Examples 2 to 6, 8, and 9

The Comparative Examples are compositions obtained by compounding 70% by weight impact-resistant polystyrene and 30% by weight propylene homopolymer with a styrene block copolymer. However, since the block copolymer does not have the structure specified in the invention, these compositions not only have considerably poor tensile elongation characteristics but also have an impaired balance among properties.

Comparative Example 7

Comparative Example 7 is an example of the same composition as in Examples 4 and 5. However, the block copolymer does not have the structure specified in the invention. Because of this, the resin composition has an impaired balance among properties.

Example 8

Ingredient (b) in Example 1 was changed from (b-1) to (b-2) to obtain a similar resin composition. The resin composition obtained had satisfactory compatibility as in Example 1.

TABLE 1

| | Structure of Block Copolymer | | | In Component Y | |
|---|---|---|---|---|---|
| Sample No. | Component X <note 1> (wt %) | Component Y <note 2> (wt %) | Vinyl bond amount before hydrogenation (wt %) | Degree of hydrogenation (%) | Residual vinyl bond amount after hydrogenation (wt %) |
| I | 66 | 34 | 50 | 0 | 50 |
| II | 66 | 34 | 50 | 26 | 29 |
| III | 66 | 34 | 50 | 44 | 3 |
| IV | 66 | 34 | 50 | 65 | 0 |
| V | 60 | 40 | 25 | 0 | 25 |
| VI | 60 | 40 | 25 | 50 | 1 |
| VII | 60 | 40 | 12 | 60 | 0 |
| VIII | 60 | 40 | 12 | 98 | 0 |
| IX | 50 | 50 | 40 | 0 | 40 |
| X | 50 | 50 | 40 | 40 | 2 |
| XI | 50 | 50 | 40 | 66 | 0 |
| XII | 66 | 34 | 48 | 60 | 1 |
| XIII | 60 | 40 | 40 | 0 | 30 |
| XIV | 60 | 40 | 40 | 52 | 1 |
| XV | 60 | 40 | 40 | 92 | 0 |
| XVI | 60 | 40 | 74 | 65 | 14 |

<note 1> polystyrene blocks
<note 2> polybutadiene block or polyisoprene block

TABLE 2

| | Resin Composition | | | | Properties | | | | | |
|---|---|---|---|---|---|---|---|---|---|---|
| | Ingredient (a) (wt %) | Ingredient (b-1) (wt %) | Ingredient (c) Kind | Ingredient (c) (parts by weight) | Tensile elongation (%) | Heat resistance (° C.) | Flexural modulus ($kg/cm^2$) | Oil resistance (° C.) | Degree of interfacial presence (%) | Thermal aging resistance |
| Ex. 1 | 70 | 30 | III | 10 | 182 | 107 | 17400 | 100 | 78 | A |
| Ex. 2 | 70 | 30 | IV | 10 | 185 | 107 | 17400 | 105 | 80 | A |
| Ex. 3 | 70 | 30 | VI | 10 | 198 | 107 | 17800 | 110 | 72 | A |
| Ex. 4 | 45 | 55 | X | 8 | 222 | 112 | 15000 | 115 | 82 | A |
| Ex. 5 | 45 | 55 | XI | 8 | 240 | 112 | 15200 | 115 | 85 | A |
| Ex. 6 | 70 | 30 | XII | 10 | 204 | 106 | 17800 | 110 | 85 | A |
| Ex. 7 | 70 | 30 | XIV | 10 | 180 | 105 | 17200 | 110 | 70 | A |

TABLE 3

| | Resin Composition | | | | Properties | | | | | |
|---|---|---|---|---|---|---|---|---|---|---|
| | Ingredient (a) (wt %) | Ingredient (b-1) (wt %) | Ingredient (c) Kind | Ingredient (c) (parts by weight) | Tensile elongation (%) | Heat resistance (° C.) | Flexural modulus ($kg/cm^2$) | Oil resistance (° C.) | Degree of interfacial presence (%) | Thermal aging resistance |
| Comp. Ex. 1 | 70 | 30 | — | 0 | 6 | 105 | 18000 | 75 | — | — |
| Comp. Ex. 2 | 70 | 30 | I | 10 | 25 | 105 | 15500 | 80 | 25 | C |

TABLE 3-continued

| | Resin Composition | | | | Properties | | | | | |
|---|---|---|---|---|---|---|---|---|---|---|
| | Ingredient (a) (wt %) | Ingredient (b-1) (wt %) | Ingredient (c) Kind | Ingredient (c) (parts by weight) | Tensile elongation (%) | Heat resistance (° C.) | Flexural modulus (kg/cm$^2$) | Oil resistance (° C.) | Degree of interfacial presence (%) | Thermal aging resistance |
| Comp. Ex. 3 | 70 | 30 | II | 10 | 64 | 105 | 15800 | 85 | 35 | B |
| Comp. Ex. 4 | 70 | 30 | V | 10 | 55 | 107 | 15500 | 85 | 25 | C |
| Comp. Ex. 5 | 70 | 30 | VII | 10 | 60 | 108 | 16400 | 85 | 35 | A |
| Comp. Ex. 6 | 70 | 30 | VIII | 10 | 50 | 108 | 16400 | 90 | 45 | A |
| Comp. Ex. 7 | 45 | 55 | IX | 8 | 62 | 110 | 14200 | 100 | 25 | C |
| Comp. Ex. 8 | 70 | 30 | XIII | 10 | 26 | 104 | 15500 | 80 | 30 | C |
| Comp. Ex. 9 | 70 | 30 | XVI | 10 | 112 | 105 | 16000 | 100 | 40 | B |

INDUSTRIAL APPLICABILITY

A thermoplastic resin composition rich in heat resistance, oil resistance, and thermal aging resistance and excellent in tensile elongation characteristics can be provided by adding a specific partially hydrogenated block copolymer to a styrene resin and/or poly(phenylene ether) resin and an olefin resin.

What is claimed is:

1. A thermoplastic resin composition which comprises (A) from 95 to 5% by weight of styrene resin and/or poly (phenylene ether) resin, (B) from 5 to 95% by weight of olefin resin, and (C) a partially hydrogenated block copolymer in an amount of from 2 to 30 parts by weight per 100 parts by weight of the sum of ingredients (A) and (B), wherein (C) is a partially hydrogenated block copolymer obtained from a block copolymer which has at least one polymer block X mainly comprising a vinylaromatic compound and at least one polymer block Y mainly comprising a conjugated diene compound and has a combined vinylaromatic compound content of from 30 to 80% by weight and in which the vinyl bond amount in the polymer block Y mainly comprising a conjugated diene compound is from 20% by weight to less than 65% by weight, by hydrogenating from 35% to 60% of the double bonds derived from the conjugated diene compounds, wherein a residual vinyl bond amount in ingredient (C) is less than 10%.

2. The thermoplastic resin composition of claim 1, wherein ingredient (A) substantially comprises a styrene resin.

3. The thermoplastic resin composition of claim 1, wherein the polymer block X mainly comprising a vinylaromatic compound is a polymer block which comprises a vinyl aromatic compound or comprises a vinylaromatic compound and a conjugated diene compound and in which the proportion of the vinylaromatic compound to the conjugated diene compound is from 100/0 to 60/40 by weight.

4. The thermoplastic resin composition of claim 1, wherein the polymer block Y mainly comprising a conjugated diene compound is a polymer block which comprises a conjugated diene compound or comprises a conjugated diene compound and vinylaromatic compound and in which the proportion of the conjugated diene compound to the vinylaromatic compound is from 100/0 to 60/40 by weight.

5. The thermoplastic resin composition of claim 1, wherein the polymer block X mainly comprising a vinylaromatic compound has a weight-average molecular weight of from 5,000 to 50,000.

6. The thermoplastic resin composition of claim 1, wherein the polymer block Y mainly comprising a conjugated diene compound has a weight-average molecular weight of from 5,000 to 70,000.

7. The thermoplastic resin composition of claim 1, wherein ingredient (A) is a styrene resin.

* * * * *